(12) United States Patent
Akihara et al.

(10) Patent No.: US 9,840,453 B2
(45) Date of Patent: Dec. 12, 2017

US009840453B2

(54) METHOD FOR PRODUCING ISOBUTYLENE, METHOD FOR PRODUCING METHACRYLIC ACID, AND METHOD FOR PRODUCING METHYL METHACRYLATE

(71) Applicant: Mitsubishi Chemical Corporation, Tokyo (JP)

(72) Inventors: Shuji Akihara, Sapporo (JP); Tatsuya Suzuki, Otake (JP); Toshiya Yasukawa, Otake (JP); Akio Takeda, Otake (JP); Kenichi Miyaki, Otake (JP); Ken Ooyachi, Otake (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/322,492

(22) PCT Filed: Jun. 26, 2015

(86) PCT No.: PCT/JP2015/068486
§ 371 (c)(1),
(2) Date: Dec. 28, 2016

(87) PCT Pub. No.: WO2016/002649
PCT Pub. Date: Jan. 7, 2016

(65) Prior Publication Data
US 2017/0129844 A1    May 11, 2017

(30) Foreign Application Priority Data
Jul. 2, 2014    (JP) .................................. 2014-136712

(51) Int. Cl.
| | | |
|---|---|---|
| C07C 67/08 | (2006.01) |
| C07C 1/24 | (2006.01) |
| C07C 51/21 | (2006.01) |
| C07C 51/235 | (2006.01) |
| C07C 29/17 | (2006.01) |
| C07C 51/25 | (2006.01) |
| C07C 51/23 | (2006.01) |

(52) U.S. Cl.
CPC ................ *C07C 67/08* (2013.01); *C07C 1/24* (2013.01); *C07C 29/172* (2013.01); *C07C 51/21* (2013.01); *C07C 51/23* (2013.01); *C07C 51/235* (2013.01); *C07C 51/252* (2013.01); *C07C 2521/04* (2013.01)

(58) Field of Classification Search
CPC .................................. C07C 1/24; C07C 1/213
See application file for complete search history.

(56) References Cited

U.S. PATENT DOCUMENTS

| | | | |
|---|---|---|---|
| 4,816,603 A | 3/1989 | Oh-Kita et al. | |
| 5,475,183 A | 12/1995 | Araki et al. | |
| 2011/0152592 A1* | 6/2011 | Cross, Jr. ................ | C07C 1/213 585/314 |
| 2011/0301316 A1* | 12/2011 | Dubois .................... | C07C 1/24 526/329.7 |

FOREIGN PATENT DOCUMENTS

| | | | |
|---|---|---|---|
| JP | 60-161932 | A | 8/1985 |
| JP | 61-22040 | A | 1/1986 |
| JP | 4-247043 | A | 9/1992 |
| JP | 4-300840 | A | 10/1992 |
| JP | 11-514337 | A | 12/1999 |
| JP | 2004-292335 | A | 10/2004 |
| JP | 2013-533236 | A | 8/2013 |
| WO | 97/03932 | A1 | 2/1997 |
| WO | 2011/085223 | A1 | 7/2011 |

OTHER PUBLICATIONS

International Search Report dated Sep. 29, 2015 in PCT/JP2015/068486 filed Jun. 26, 2015.
Joshua D. Taylor et al., "Dehydration of Fermented Isobutanol for the Production of Renewable Chemicals and Fuels", Topics in Catalysis, 2010, vol. 53, pp. 1224-1230.

* cited by examiner

*Primary Examiner* — Paul A Zucker
(74) *Attorney, Agent, or Firm* — Oblon, McClelland, Maier & Neustadt, L.L.P.

(57) ABSTRACT

Provided is a method for producing isobutylene with a high selectivity by a dehydration reaction of isobutanol. There are provided a method for producing isobutylene by dehydration of isobutanol, in which the dehydration of isobutanol is performed in a state where at least one of an organic acid and an organic acid ester is present in a reaction system, and methods for producing methacrylic acid and methyl methacrylate from the obtained isobutylene.

19 Claims, No Drawings

METHOD FOR PRODUCING ISOBUTYLENE, METHOD FOR PRODUCING METHACRYLIC ACID, AND METHOD FOR PRODUCING METHYL METHACRYLATE

TECHNICAL FIELD

The present invention relates to a method for producing isobutylene from isobutanol, particularly, from biomass-derived isobutanol. In addition, the invention relates to methods for producing methacrylic acid and methyl methacrylate using the isobutylene.

BACKGROUND ART

Isobutylene is one of important chemical raw materials which are converted into ethyl tert-butyl ether (ETBE), paraxylene, or methyl methacrylate (MMA) monomer. Of them, for example, a MMA monomer is a substance that is highly useful as a raw material of poly methyl methacrylate useful as a transparent resin. As one of methods for producing this MMA monomer, a method of synthesizing isobutylene as a starting material is mentioned.

Isobutylene as a raw material of the MMA monomer is obtained by extracting isobutylene as tert-butanol through a hydration reaction with an acid catalyst from the spent BB, which is a residue derived by fractional distillation of butadiene from the $C_4$ fraction obtained by naphtha cracking, and then by dehydrating tert-butanol. Further, a method in which methyl tert-butyl ether is synthesized once from isobutylene in the spent BB and methanol and then decomposing this methyl tert-butyl ether is also mentioned. In such a currently used method for producing isobutylene, petroleum is used as a raw material. Therefore, in the circumstance in which there is a concern of depletion problem of petroleum in recent years, a novel method with no dependence on petroleum is desired.

Further, carbon dioxide generated when petroleum is combusted is considered to cause global warming. In this regard, as technologies for producing energy and chemical products from a biomass that is a renewable resource, a biorefinery technology has attracted attention worldwide. Biorefinery means that synthesis gas, sugars such as glucose, aromatic compounds such as lignin, and the like are produced by gasification, glycosylation, and extraction of various biomasses, and these obtained products are variedly converted to produce energy and chemical products. As products produced by biorefinery, as energy, ethanol, butanol, diesel oil, or the like is mentioned. Also for chemical products, according to derivation from a key compound (platform compound) such as sugar-derived succinic acid, 3-hydroxypropionic acid, or asparagine acid, which is suggested by United States Department of Energy, various chemical products can be produced.

Further, it is known that isobutanol can also be produced by fermentation of glucose, and isobutanol is mentioned as one of biomass-derived raw materials. For example, in Patent Literature 1, Patent Literature 2, and Non-Patent Literature 1, it is described that isobutylene can be produced by dehydration of isobutanol.

CITATION LIST

Patent Literature

Patent Literature 1: WO 2011/085223 A
Patent Literature 2: JP 4-247043 A

Non-Patent Literature

Non-Patent Literature 1: Topics in Catalysis (2010) 53, 1224-1230

SUMMARY OF THE INVENTION

Problem to be Solved by the Invention

Isobutylene is produced by dehydration of isobutanol using, as each dehydration catalyst, γ-alumina or zeolite in Patent Literature 1, γ-alumina in Non-Patent Literature 1, and γ-alumina containing silica in Patent Literature 2. However, the selectivity of isobutylene in the gas component after the reaction is not always sufficient.

In order to suppress production costs of isobutylene, it is necessary to perform a dehydration reaction with a higher selectivity. Furthermore, in order to efficiently utilize a raw material for the purpose of reducing environmental load, it is also important to increase selectivity from isobutanol to isobutylene by employing a process of recovering unreacted isobutanol and recycling the recovered unreacted isobutanol as a raw material to a reactor, even when a conversion rate of isobutanol serving as the raw material is low.

The invention is made to solve such problems. That is, an object of the invention is to provide a method by which isobutylene can be produced with a high selectivity by a dehydration reaction of isobutanol.

Means for Solving Problem

A method for producing isobutylene according to the invention is a method for producing isobutylene by dehydration of isobutanol, in which the dehydration of isobutanol is performed in a state where at least one of an organic acid and an organic acid ester is present in a reaction system.

A method for producing methacrylic acid according to the invention is a method for producing methacrylic acid, including a step of producing isobutylene by the method for producing isobutylene according to the invention, and a step of producing methacrylic acid by subjecting the isobutylene to vapor phase catalytic oxidation with molecular oxygen.

A method for producing methacrylic acid according to the invention is a method for producing methacrylic acid, including a step of producing isobutylene by the method for producing isobutylene according to the invention, a step of producing tert-butyl alcohol by subjecting the isobutylene to hydration in the presence of an acid catalyst, and a step of producing methacrylic acid by subjecting the tert-butyl alcohol to vapor phase catalytic oxidation with molecular oxygen.

A method for producing methyl methacrylate according to the invention is a method for producing methyl methacrylate, including a step of producing methacrylic acid by the method of producing methacrylic acid according to the invention, and a step of producing methyl methacrylate by subjecting the methacrylic acid to an esterification reaction with methanol in the presence of an acid catalyst.

Effect of the Invention

According to the invention, it is possible to produce isobutylene with a high selectivity by a dehydration reaction of isobutanol.

MODE(S) FOR CARRYING OUT THE INVENTION

[Method for Producing Isobutylene]

A method for producing isobutylene according to the invention is a method for producing isobutylene by dehydration of isobutanol, in which the dehydration of isobutanol is performed in a state where at least one of organic acids and organic acid esters is present in a reaction system. When at least one of organic acids and organic acid esters is allowed to be present in the reaction system, it is possible to produce isobutylene with a high selectivity in a dehydration reaction of isobutanol.

In the method according to the invention, isobutylene is produced by the dehydration reaction of isobutanol. There is no particular limitation on isobutanol serving as a starting material. However, it is preferable that the isobutanol includes biomass-derived isobutanol. In the invention, since isobutylene can be produced with a high selectivity using the biomass-derived isobutanol as a starting material, the biomass-derived isobutanol is particularly useful from the viewpoint of environmental protection. The biomass-derived isobutanol indicates a compound purified from an organic compound obtained by using a biomass fermentable sugar and performing a fermentation process of the biomass fermentable sugar or isobutanol obtained by a step including at least one of catalyst chemical conversion and thermal chemical conversion of a biomass. The biomass is largely classified into a biomass derived from resource crops and a biomass derived from wastes. Examples of the biomass derived from resource crops include edible crops, woods, grasses and flowers. In addition to these, unused portions of these crops can also be used. Meanwhile, examples of the biomass derived from wastes include food wastes, sludge of sewage or the like, livestock excreta, and waste paper. In addition, as isobutanol serving as a starting material, it is also possible to mix fossil-derived isobutanol and biomass-derived isobutanol for use.

The dehydration reaction of isobutanol may be performed by any of a liquid phase and a gas phase. When the reaction is performed by a gas phase, the type of a gas phase reaction represented by a fixed bed or a fluidized bed can be used. Hereinafter, a case in which the reaction is performed by a gas phase will be described, but the invention is not limited thereto.

In the method according to the invention, at least one of organic acids and organic acid esters is allowed to be present in a reaction system. Only organic acids may be allowed to be present in the reaction system, only organic acid esters may be allowed to be present in the reaction system, or both of organic acids and organic acid esters may be allowed to be present in the reaction system. From the viewpoint of sufficiently improving the selectivity of isobutylene, a content of the organic acid and the organic acid ester in the reaction system is preferably 0.005% by mass or more with respect to a total of the mass of the isobutanol and the mass of the organic acid and the organic acid ester, more preferably 0.01% by mass or more, and still more preferably 0.02% by mass or more. In addition, from the viewpoint that costs for separation and purification can be reduced, the content of the organic acid and the organic acid ester in the reaction system is preferably 10% by mass or less with respect to the total of the mass of the isobutanol and the mass of the organic acid and the organic acid ester, more preferably 8% by mass or less, and still more preferably 5% by mass or less. The content of the organic acid and the organic acid ester with respect to the total of the mass of the isobutanol and the mass of the organic acid and the organic acid ester is defined as follows.

Content (%) of the organic acid and the organic acid ester with respect to the total of the mass of the isobutanol and the mass of the organic acid and the organic acid ester=Mass of the organic acid and the organic acid ester/(Mass of the isobutanol+Mass of the organic acid and the organic acid ester)×100

There is no particular limitation on a method for allowing at least one of the organic acid and the organic acid ester to be present in the reaction system. At least one of the organic acids and the organic acid esters may be contained in isobutanol and then supplied into the reaction system, or at least one of the organic acids and the organic acid esters may be supplied from each line into the reaction system without mixed with isobutanol.

Examples of the organic acids include mono- and poly-carboxylic acids. Examples of the organic acids include carboxylic acids such as saturated aliphatic carboxylic acids, unsaturated aliphatic carboxylic acids, alicyclic carboxylic acids, and aromatic carboxylic acids. Specific examples of the organic acids include formic acid, acetic acid, propionic acid, butyric acid, valeric acid, caproic acid, enanthic acid, caprylic acid, pelargonic acid, capric acid, acrylic acid, methacrylic acid, benzoic acid, toluic acid, anisic acid, succinic acid, malonic acid, maleic acid, itaconic acid, phthalic acid isophthalic acid, and terephthalic acid. From the viewpoint of improving the selectivity of isobutylene, as the organic acids, formic acid, acetic acid, propionic acid, butyric acid, valeric acid, benzoic acid, terephthalic acid, and methacrylic acid are preferable, and acetic acid, propionic acid, butyric acid, valeric acid, and methacrylic acid are more preferable. These organic acids may be used singly or in combination of two or more kinds thereof.

Examples of the organic acid esters include mono- and poly-carboxylate esters. Examples of the organic acid esters include carboxylate esters such as saturated aliphatic carboxylate esters, unsaturated aliphatic carboxylate esters, alicyclic carboxylate esters, and aromatic carboxylate esters. Specific examples of the organic acid esters include formate esters such as methyl formate, ethyl formate, propyl formate, butyl formate, and isobutyl formate; acetate esters such as methyl acetate, ethyl acetate, n-butyl acetate, isobutyl acetate, tert-butyl acetate, and phenyl acetate; propionate esters such as methyl propionate, ethyl propionate, propyl propionate, n-butyl propionate, isobutyl propionate, and tert-butyl propionate; butyrate esters such as methyl butyrate, ethyl butyrate, propyl butyrate, n-butyl butyrate, and isobutyl butyrate; valerate esters such as methyl valerate, ethyl valerate, propyl valerate, n-butyl valerate, and isobutyl valerate; caproate esters such as methyl caproate, ethyl caproate, propyl caproate, n-butyl caproate, and isobutyl caproate; enanthate esters such as methyl enanthate, ethyl enanthate, propyl enanthate, n-butyl enanthate, and isobutyl enanthate; caprylate esters such as methyl caprylate, ethyl caprylate, propyl caprylate, n-butyl caprylate, and isobutyl caprylate; pelargonate esters such as methyl pelargonate, ethyl pelargonate, propyl pelargonate, n-butyl pelargonate, and isobutyl pelargonate; caprate esters such as methyl caprate, ethyl caprate, propyl caprate, n-butyl caprate, and isobutyl caprate; acrylate esters such as methyl acrylate, ethyl acrylate, propyl acrylate, n-butyl acrylate, and isobutyl acrylate; methacrylate esters such as methyl methacrylate, ethyl methacrylate, propyl methacrylate, n-butyl methacrylate, and isobutyl methacrylate; benzoate esters such as methyl benzoate, ethyl benzoate, propyl benzoate, n-butyl benzoate, isobutyl benzoate, and tert-butyl benzoate; toluate esters such as methyl toluate and ethyl toluate; anisate esters such as methyl anisate and ethyl anisate; succinate esters such as dimethyl succinate, diethyl succinate, and di-n-butyl succinate; malonate esters such as dimethyl malonate, diethyl malonate, and di-n-butyl malonate; maleate esters such as dimethyl maleate and dibutyl maleate; itaconate esters such as diethyl itaconate and di-n-butyl itaconate; phthalate esters such as monoethyl phthalate, dimethyl phthalate, methyl ethyl phthalate, diethyl phthalate, di-n-propyl phthalate, diisopropyl phthalate, di-n-butyl phthalate, diisobutyl phthalate, di-tert-butyl phthalate, dipentyl phthalate, di-n-hexyl phthalate, diheptyl phthalate, di-n-octyl phthalate, di(2-ethylhexyl) phthalate, diisodecyl phthalate, dicyclohexyl phthalate, and diphenyl phthalate; isophthalate esters such as dimethyl isophthalate, diethyl isophthalate, di-n-butyl isophthalate, diisobutyl isophthalate, and di-tert-butyl isophthalate; and terephthalate esters such as dimethyl terephthalate, diethyl terephthalate, di-n-butyl terephthalate, diisobutyl terephthalate, and di-tert-butyl terephthalate. From the viewpoint of improving the selectivity of isobutylene, as the organic acid esters, acetate esters, propionate esters, butyrate esters, valerate esters, and methacrylate esters are preferable, methyl acetate, ethyl acetate, isobutyl acetate, tert-butyl acetate, methyl propionate, ethyl propionate, isobutyl propionate, tert-butyl propionate, methyl butyrate, ethyl butyrate, propyl butyrate, n-butyl butyrate, isobutyl butyrate, methyl valerate, ethyl valerate, propyl valerate, n-butyl valerate, isobutyl valerate, methyl methacrylate, ethyl methacrylate, propyl methacrylate, n-butyl methacrylate, and isobutyl methacrylate are more preferable, and ethyl acetate, isobutyl acetate, and tert-butyl acetate are still more preferable. These organic acid esters may be used singly or in combination of two or more kinds thereof.

It is preferable that the raw material is evaporated in advance and then supplied to a reactor. The evaporator used for evaporating the raw material is not particularly limited. As the evaporator, for example, various evaporators of a jacket type, a natural circulation horizontal tube type, a natural circulation immersed tube type, a natural circulation vertical short tube type, a vertical long tube climbing film type, a horizontal tube falling film type, a forced circulation horizontal tube type, a forced circulation vertical tube type, a coil type, and the like can be used. Further, a heating coil is wound around a pipe, the raw material is evaporated in a raw material supply pipe before the raw material is input to the reactor, and then the raw material in a gas state can also be supplied to the reactor. Furthermore, even when a component other than the raw material is evaporated and then supplied to the reactor, there is no particular limitation on the evaporator.

When isobutanol serving as a raw material is supplied to the reactor, the concentration of isobutanol in the reaction gas can be adjusted by using a dilution gas. The type of the dilution gas is not particularly limited. As the dilution gas, nitrogen, helium, neon, krypton, xenon, radon, argon, methane, ethane, propane, butane, isobutane, carbon monoxide, carbon dioxide, nitrogen monoxide, nitrogen dioxide, nitrous oxide, dinitrogen trioxide, dinitrogen tetroxide, dinitrogen pentoxide, and water vapor are preferable. In addition, oxygen can be used as a dilution gas as long as the concentration thereof is out of an explosive range and is such a concentration that does not allow the side reaction to be significantly promoted. Further, hydrogen can be used as a dilution gas as long as the concentration thereof is such a concentration that does not allow the side reaction to be significantly promoted in a concentration range that enables the operation to be safely performed. These dilution gases may be used singly or in combination of two or more kinds thereof.

In the method according to the invention, the concentration of isobutanol in the reaction gas to be supplied to the reactor can be freely set. The reaction pressure is preferably normal pressure to 1 MPaG and more preferably normal pressure to 0.5 MPaG. With such a range, isobutylene can be produced with a high yield and there is also an economic advantage in terms of facilities. The reaction temperature (the temperature in a catalyst layer during the reaction) can be selected from the range of 108 to 500° C., but from the viewpoint of sufficiently obtaining the effect of the invention, the reaction temperature is preferably 115 to 415° C. and more preferably 150 to 400° C. When the reaction temperature is 108° C. or higher, reaction activity is improved, and thus there is no need that the amount of the dehydration catalyst is increased or the supply rate of the reaction gas is decreased. In addition, when the reaction temperature is 500° C. or lower, the reaction speed of an isomerization reaction is decreased and the selectivity of isobutylene is improved. The method for controlling the reaction temperature is not particularly limited. Herein, the reaction temperature is defined as the lowest temperature of the catalyst layer that can be confirmed after steady state is achieved. Therefore, when the temperature distribution is present in the catalyst layer, a measurement point can be increased or the temperature can be continuously measured in a catalyst charge direction.

The dehydration reaction of isobutanol is preferably performed by using a dehydration catalyst such as an acid catalyst. Examples of the acid catalyst include alumina, silica alumina, solid phosphoric acid, titania, and zirconia. These may be used singly or in combination of two or more kinds thereof. Particularly, from the viewpoint of the selectivity of isobutylene, alumina is preferable as a dehydration catalyst. There is no particular limitation on the crystalline form of alumina, and for example, α-alumina, β-alumina, γ-alumina, σ-alumina, an alumina hydrate, and the like are mentioned. These may be used singly or in combination of two or more kinds thereof. Particularly, from the viewpoint of activity and the selectivity of isobutylene, a catalyst containing γ-alumina is preferable as a dehydration catalyst.

Alumina can be produced by a known method and the production method therefor is not particularly limited. Alumina can be easily produced, for example, by a thermal decomposition method, a precipitation method, a deposition method, a kneading method, or a method of concurrently using these methods. Examples of the raw material of alumina include materials that produce alumina or an alumina hydrate by heating or hydrolysis, such as nitrate salt, acetate salt, alkoxide, sulfate salt, chloride, alkaline aluminate, and alum. Examples of alkali to be used in a hydrolysis reaction include caustic alkali, alkaline carbonate, ammonia water, and ammonium carbonate. These may be used singly or in combination of two or more kinds thereof.

Alumina obtained by the method as described above may be molded and used as a dehydration catalyst, as necessary. For example, in the case of a gas phase fixed-bed reaction, the shape of a molded body of alumina is preferably determined in consideration of pressure drop or gas diffusion in the reactor. Further, in any cases of a gas phase fluidized-bed reaction and a liquid phase reaction, the shape of a molded body of alumina is preferably determined in consideration of reaction conditions or mass transfer. As the method for molding alumina, for example, there is mentioned a method for forming alumina in an arbitrary shape, such as a spherical shape, a ring shape, a cylindrical shape, or a star shape, by using a powder molding machine such as a tablet molding machine, an extrusion molding machine, or a tumbling granulator. In addition, the alumina thus obtained may be ground to be used as powder. Further, an additive such as a polymer compound (for example, polyvinyl alcohol), an α-glucan derivative, or a β-glucan derivative may be mixed with alumina before molding, as necessary.

W/F that is a ratio of the catalyst mass to the flow velocity of the reaction gas is preferably 0.0050 to 2.0 g·hr/NL (normal liter) and more preferably 0.01 to 1.5 g·hr/NL (normal liter). When W/F is 0.0050 g·hr/NL or more, the conversion rate of isobutanol is improved and the recovery costs for unreacted isobutanol can be decreased. In addition, when W/F is 2.0 g·hr/NL or less, the selectivity and the yield of isobutanol are improved.

[Method for Producing Methacrylic Acid]

A method for producing methacrylic acid according to the invention includes a step of producing isobutylene by the method for producing isobutylene and a step of producing methacrylic acid by subjecting the isobutylene to vapor phase catalytic oxidation with molecular oxygen.

In addition, a method for producing methacrylic acid according to the invention includes a step of producing isobutylene by the method for producing isobutylene, a step of producing tert-butyl alcohol by subjecting the isobutylene to hydration in the presence of an acid catalyst, and a step of producing methacrylic acid by subjecting the tert-butyl alcohol to vapor phase catalytic oxidation with molecular oxygen.

According to these methods, it is possible to produce methacrylic acid from isobutylene with a high selectivity.

When a hydration reaction of isobutylene is performed, the hydration reaction of isobutylene can be performed according to a known method, but in particular, is preferably performed by using a hydration catalyst such as an acid catalyst. Specific examples of the acid catalyst include ion-exchange resins and heteropoly acids. From the viewpoint that tert-butyl alcohol can be produced with a high yield, as an acid catalyst, a strongly acidic cation-exchange resin is preferable. The reaction temperature is preferably 30 to 100° C.

The vapor phase catalytic oxidation of isobutylene or tert-butyl alcohol with molecular oxygen can be performed by single-step or two-step vapor phase catalytic oxidation. The vapor phase catalytic oxidation is preferably two-step vapor phase catalytic oxidation from the viewpoint that methacrylic acid can be produced from isobutylene with a higher selectivity.

When the vapor phase catalytic oxidation is performed at two steps, as a first oxidation reaction catalyst to be used in a first vapor phase catalytic oxidation (first oxidation reaction), a known catalyst can be used, but a catalyst containing at least molybdenum and bismuth is preferable. The catalyst may contain, as a catalyst component other than molybdenum and bismuth, for example, iron, silicon, cobalt, nickel, chromium, lead, manganese, calcium, magnesium, niobium, silver, barium, tin, tantalum, zinc, phosphorus, boron, sulfur, selenium, tellurium, cerium, tungsten, antimony, titanium, lithium, sodium, potassium, rubidium, cesium, thallium, or the like. Particularly, a catalyst having a composition represented by the following Formula (A) is preferable.

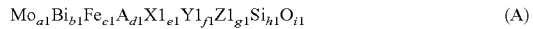

$$Mo_{a1}Bi_{b1}Fe_{c1}A_{d1}X1_{e1}Y1_{f1}Z1_{g1}Si_{h1}O_{i1} \quad (A)$$

In Formula (A), each of Mo, Bi, Fe, Si, and O represents molybdenum, bismuth, iron, silicon, and oxygen. A represents at least one element selected from the group consisting of cobalt and nickel. X1 represents at least one element selected from the group consisting of chromium, lead, manganese, calcium, magnesium, niobium, silver, barium, tin, tantalum, and zinc. Y1 represents at least one element selected from the group consisting of phosphorus, boron, sulfur, selenium, tellurium, cerium, tungsten, antimony, and titanium. Z1 represents at least one element selected from the group consisting of lithium, sodium, potassium, rubidium, cesium, and thallium. Each of a1, b1, c1, d1, e1, f1, g1, h1, and i1 represents an atomic ratio of each element, when a1=12, b1=0.01 to 3, c1=0.01 to 5, d1=1 to 12, e1=0 to 8, f1=0 to 5, g1=0.001 to 2, and h1=0 to 20, and i1 is an atomic ratio of oxygen necessary for satisfying an atomic valence of each component described above.

The first oxidation reaction can be performed by a fixed bed. The catalyst layer is not particularly limited, and the catalyst layer may be an undiluted layer containing only a catalyst or a diluted layer containing an inert carrier. In addition, the catalyst layer may be a single layer or a mixed layer formed by a plurality of layers.

The concentration of isobutylene or tert-butyl alcohol serving as a raw material in a raw material gas is not particularly limited, but is preferably 1 to 20% by volume. Any one of isobutylene and tert-butyl alcohol may be used, or both of isobutylene and tert-butyl alcohol may be used in combination. As a molecular oxygen source, use of air is economic, but if necessary, air enriched with pure oxygen, or the like can be used. The molar ratio (volume ratio) of the raw material to oxygen in the raw material gas is preferably in a range of 1:0.5 to 1:3.

The raw material gas preferably contains water (water vapor) in addition to the raw material and molecular oxygen. The concentration of water vapor in the raw material gas is preferably 1 to 45% by volume. In addition, the raw material gas is preferably used by being diluted with an inert gas such as nitrogen or carbon dioxide. The reaction pressure is preferably atmospheric pressure to 200 kPaG The reaction temperature is preferably 200 to 450° C. and more preferably 250 to 400° C. The contact time is preferably 1.5 to 15 seconds and more preferably 2 to 10 seconds.

Methacrolein and methacrylic acid are obtained by the first oxidation reaction. This methacrolein is converted into methacrylic acid by the second vapor phase catalytic oxidation (second oxidation reaction).

As a second oxidation reaction catalyst to be used in the second oxidation reaction, a known catalyst can be used, but a catalyst containing at least molybdenum and phosphorus is preferable. Particularly, a catalyst having a composition represented by the following Formula (B) is preferable.

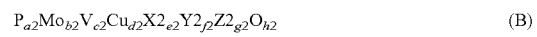

$$P_{a2}Mo_{b2}V_{c2}Cu_{d2}X2_{e2}Y2_{f2}Z2_{g2}O_{h2} \quad (B)$$

In the above Formula (B), each of P, Mo, V, Cu, and O represents phosphorus, molybdenum, vanadium, copper, and oxygen. X2 represents at least one element selected from the group consisting of arsenic, antimony, and tellurium. Y2 represents at least one element selected from the group consisting of bismuth, germanium, zirconium, silver, selenium, silicon, tungsten, boron, iron, zinc, chromium, magnesium, tantalum, cobalt, manganese, barium, gallium, cerium, and lanthanum. Z2 represents at least one element selected from the group consisting of potassium, rubidium, and cesium. Each of a2, b2, c2, d2, e2, f2, g2, and h2 represents an atomic ratio of each element, when b2=12, a2=0.1 to 3, c2=0.01 to 3, d2=0.01 to 2, e2=0 to 3, f2=0 to 3, and g2=0.01 to 3, and h2 is an atomic ratio of oxygen necessary for satisfying an atomic valence of each component described above.

The second oxidation reaction can be performed by a fixed bed. The catalyst layer is not particularly limited, and the catalyst layer may be an undiluted layer containing only a catalyst or a diluted layer containing an inert carrier. In addition, the catalyst layer may be a single layer or a mixed layer formed by a plurality of layers.

The concentration of methacrolein serving as a raw material in the raw material gas can be changed within a wide range, but is preferably 1% by volume or more and more preferably 3% by volume or more. In addition, the concentration of methacrolein serving as a raw material in the raw material gas is preferably 20% by volume or less and more preferably 10% by volume or less. The concentration of molecular oxygen in the raw material gas is preferably 0.4 mol or more and more preferably 0.5 mol or more per 1 mol of methacrolein. Further, the concentration of molecular oxygen in the raw material gas is preferably 4 mol or less and more preferably 3 mol or less per 1 mol of methacrolein. As a molecular oxygen source, use of air is economic, but if necessary, air enriched with pure oxygen, or the like can be used.

The raw material gas preferably contains water (water vapor) in addition to methacrolein and molecular oxygen. When the reaction is performed in the presence of water, methacrylic acid is obtained with a higher yield. The concentration of water vapor in the raw material gas is preferably 0.1% by volume or more and more preferably 1% by volume or more. In addition, the concentration of water vapor in the raw material gas is preferably 50% by volume or less and more preferably 40% by volume or less. The raw material gas may contain a small amount of impurities such as lower saturated aldehyde, but the amount thereof is preferably as small as possible. Further, the raw material gas may contain an inert gas such as nitrogen or carbon dioxide.

The reaction pressure is preferably in a range of normal pressure (atmospheric pressure) to 500 kPaG The reaction temperature is preferably 230° C. or higher and more preferably 250° C. or higher. In addition, the reaction temperature is preferably 450° C. or lower and more preferably 400° C. or lower. The flow rate of the raw material gas is not particularly limited, and can be appropriately set such that the contact time becomes proper. The contact time is preferably 1.5 seconds or longer and more preferably 2 seconds or longer. In addition, the contact time is preferably 15 seconds or shorter and more preferably 10 seconds or shorter.

[Method for Producing Methyl Methacrylate]

A method for producing methyl methacrylate according to the invention includes a step of producing methacrylic acid by the method of producing methacrylic acid and a step of producing methyl methacrylate by subjecting the methacrylic acid to an esterification reaction with methanol in the presence of an acid catalyst. According to the method, methyl methacrylate can be produced from isobutylene with a high selectivity. For example, methyl methacrylate can be produced by recovering methacrylic acid, which is produced by the above-described method, by extraction or distillation operation and subjecting the methacrylic acid to an esterification reaction with methanol in the presence of an acid catalyst.

As a catalyst of the esterification reaction, sulfuric acid or an ion-exchange resin can be used. As the ion-exchange resin, a strongly acidic cation-exchange resin is preferably used. Specific examples of the strongly acidic cation-exchange resin include DIAION (registered trademark), PK216, and RCP12H (manufactured by Mitsubishi Chemical Corporation); Lewatit (registered trademark) and K2431 (manufactured by Bayer AG); and AMBERLYST (registered trademark) 15WET (manufactured by Rohm & Haas Japan Co., Ltd.). These may be used singly or in combination of two or more kinds thereof.

The flow direction of the reaction fluid may be a vertically upward direction or a vertically downward direction, and is appropriately selected. When an ion-exchange resin is used as a catalyst and swelling of the ion-exchange resin is large, the flow direction of the reaction fluid is preferably the vertically upward direction. Further, when the reaction fluid forms a heterogeneous phase, the flow direction of the reaction fluid is preferably the vertically downward direction.

When a fixed bed type reactor is charged with the ion-exchange resin and then the reaction is performed, the flowing amount of the raw material is not particularly limited, but the flowing amount of the raw material is preferably 0.1 mass time or more and more preferably 0.2 mass time or more the amount of the ion-exchange resin. Further, the flowing amount of the raw material is preferably 10 mass time or less and more preferably 5 mass time or less the amount of the ion-exchange resin.

When the strongly acidic cation-exchange resin is used as a catalyst, the reaction temperature is preferably within a range of 40 to 130° C. As the reaction temperature is increased, the reaction speed is increased and the reaction can be efficiently carried out. As the reaction temperature is decreased, the deterioration rate of the ion-exchange resin is decreased and the reaction can be continuously carried out for a long period of time. In the case of the esterification reaction, from the viewpoint of chemical equilibrium, the optimal reaction temperature is appropriately determined. Further, regarding the raw material composition, from the viewpoint of chemical equilibrium, the concentration of any one of methacrylic acid and methanol is increased and the conversion rate of the raw material having a lower concentration is increased. According to this, processes of recovery and purification steps can be simplified.

EXAMPLES

Hereinafter, the invention will be described in detail by means of Examples. However, the invention is not limited to these Examples. The analyses of a raw material gas and a product were performed using gas chromatography. The conversion rate of isobutanol and the selectivity of isobutylene to be produced are defined as follows, respectively.

Conversion rate (%) of isobutanol=$(\beta/\alpha) \times 100$

Selectivity (%) of isobutylene=$(\gamma/\delta) \times 100$

α: Molar number of supplied isobutanol

β: Molar number of reacted isobutanol

γ: Molar number of produced isobutylene

δ: Total molar number of reaction products (isobutylene, isobutane, 1-butene, cis-2-butene, and trans-2-butene) detected by gas chromatography Example 1

0.01 g of isobutyl acetate (manufactured by Wako Pure Chemical Industries, Ltd., a purity of 98.0% by mass) was mixed with 50 g of isobutanol (manufactured by Wako Pure Chemical Industries, Ltd., a purity of 99.5% by mass) to prepare an isobutanol mixed solution containing 0.02% by mass of isobutyl acetate with respect to isobutanol.

As a dehydration catalyst, γ-alumina (trade name: SA3177, manufactured by Saint-Gobain SA) was used. A fixed bed reactor (inner diameter: 16.3 mm, length: 500 mm)

immersed in a heating medium was charged with 1.40 g of the dehydration catalyst, and the temperature of the heating medium was adjusted to 340° C. Then, the flow rate of the isobutanol mixed solution was adjusted to 4.13 g/hr by using a pump and supplied to an evaporator set at 200° C. to obtain an isobutanol-mixed gas. Further, nitrogen gas was supplied as a dilution gas at a flow rate of 17 NL/hr to the evaporator. As a result, the raw material gas composition supplied to the fixed bed reactor was 5% by volume of isobutanol-mixed gas and 95% by volume of nitrogen, and W/F was 0.077 g·hr/NL.

The gas at the outlet side of the reactor was collected and quantitative determination of isobutylene, isobutane, 1-butene, cis-2-butene, and trans-2-butene was performed using gas chromatography. Further, unreacted isobutanol was trapped by using acetonitrile obtained by ice cooling the reaction gas discharged from the outlet side of the reactor and then quantitative determination thereof was performed using gas chromatography.

Example 2

The same operation as in Example 1 was conducted, except that 0.05 g of isobutyl acetate was mixed with 50 g of isobutanol to prepare an isobutanol mixed solution containing 0.10% by mass of isobutyl acetate with respect to isobutanol.

Example 3

The same operation as in Example 1 was conducted, except that 0.25 g of isobutyl acetate was mixed with 50 g of isobutanol to prepare an isobutanol mixed solution containing 0.49% by mass of isobutyl acetate with respect to isobutanol.

Example 4

The same operation as in Example 1 was conducted, except that 1.0 g of isobutyl acetate was mixed with 50 g of isobutanol to prepare an isobutanol mixed solution containing 1.93% by mass of isobutyl acetate with respect to isobutanol.

Example 5

The same operation as in Example 1 was conducted, except that 1.5 g of isobutyl acetate was mixed with 50 g of isobutanol to prepare an isobutanol mixed solution containing 2.87% by mass of isobutyl acetate with respect to isobutanol.

Example 6

The same operation as in Example 1 was conducted, except that 2.5 g of isobutyl acetate was mixed with 50 g of isobutanol to prepare an isobutanol mixed solution containing 4.69% by mass of isobutyl acetate with respect to isobutanol.

Example 7

The same operation as in Example 1 was conducted, except that 3.5 g of isobutyl acetate was mixed with 50 g of isobutanol to prepare an isobutanol mixed solution containing 6.45% by mass of isobutyl acetate with respect to isobutanol.

Example 8

The same operation as in Example 1 was conducted, except that 5.0 g of isobutyl acetate was mixed with 50 g of isobutanol to prepare an isobutanol mixed solution containing 8.97% by mass of isobutyl acetate with respect to isobutanol.

Example 9

The same operation as in Example 1 was conducted, except that 2.5 g of tert-butyl acetate (manufactured by Wako Pure Chemical Industries, Ltd., a purity of 98.0%) was mixed with 50 g of isobutanol to prepare an isobutanol mixed solution containing 4.69% by mass of tert-butyl acetate with respect to isobutanol.

Example 10

The same operation as in Example 1 was conducted, except that 1.5 g of ethyl acetate (manufactured by KANTO CHEMICAL CO INC., a purity of 99.5%) was mixed with 50 g of isobutanol to prepare an isobutanol mixed solution containing 2.91% by mass of ethyl acetate with respect to isobutanol.

Example 11

The same operation as in Example 1 was conducted, except that 0.25 g of acetic acid (manufactured by KANTO CHEMICAL CO., INC., a purity of 99.7%) was mixed with 50 g of isobutanol to prepare an isobutanol mixed solution containing 0.50% by mass of acetic acid with respect to isobutanol.

Example 12

The same operation as in Example 1 was conducted, except that 1.0 g of acetic acid was mixed with 50 g of isobutanol to prepare an isobutanol mixed solution containing 1.96% by mass of acetic acid with respect to isobutanol.

Example 13

The same operation as in Example 1 was conducted, except that 2.5 g of acetic acid was mixed with 50 g of isobutanol to prepare an isobutanol mixed solution containing 4.77% by mass of acetic acid with respect to isobutanol.

Example 14

The same operation as in Example 1 was conducted, except that 1.5 g of propionic acid (manufactured by KANTO CHEMICAL CO., INC., a purity of 99.0%) was mixed with 50 g of isobutanol to prepare an isobutanol mixed solution containing 2.90% by mass of acetic acid with respect to isobutanol.

Example 15

The same operation as in Example 1 was conducted, except that 1.5 g of valeric acid (manufactured by Tokyo Chemical Industry Co., Ltd., a purity of 98.0%) was mixed with 50 g of isobutanol to prepare an isobutanol mixed solution containing 2.87% by mass of valeric acid with respect to isobutanol.

Example 16

The same operation as in Example 1 was conducted, except that 1.5 g of methacrylic acid (manufactured by Wako Pure Chemical Industries, Ltd., a purity of 99.7%) was mixed with 50 g of isobutanol to prepare an isobutanol mixed solution containing 2.92% by mass of methacrylic acid with respect to isobutanol.

Example 17

The same operation as in Example 1 was conducted, except that 0.75 g of methacrylic acid (manufactured by Wako Pure Chemical Industries, Ltd., a purity of 99.7%) and 0.75 g of ethyl acetate (manufactured by KANTO CHEMICAL CO., INC., a purity of 99.5%) were mixed with 50 g of isobutanol to prepare an isobutanol mixed solution containing 1.46% by mass of methacrylic acid and 1.46% by mass of ethyl acetate with respect to isobutanol.

Example 18

The same operation as in Example 1 was conducted, except that 0.75 g of acetic acid (manufactured by KANTO CHEMICAL CO., INC., a purity of 99.7%) and 0.75 g of isobutyl acetate (manufactured by Wako Pure Chemical Industries, Ltd., a purity of 98.0% by mass) were mixed with 50 g of isobutanol to prepare an isobutanol mixed solution containing 1.46% by mass of acetic acid and 1.43% by mass of isobutyl acetate with respect to isobutanol.

Example 19

The same operation as in Example 1 was conducted, except that 1.25 g of acetic acid (manufactured by KANTO CHEMICAL CO., INC., a purity of 99.7%) and 0.25 g of isobutyl acetate (manufactured by Wako Pure Chemical Industries, Ltd., a purity of 98.0% by mass) were mixed with 50 g of isobutanol to prepare an isobutanol mixed solution containing 2.43% by mass of acetic acid and 0.48% by mass of isobutyl acetate with respect to isobutanol.

Example 20

The same operation as in Example 1 was conducted, except that 0.25 g of acetic acid (manufactured by KANTO CHEMICAL CO INC., a purity of 99.7%) and 1.25 g of isobutyl acetate (manufactured by Wako Pure Chemical Industries, Ltd., a purity of 98.0% by mass) were mixed with 50 g of isobutanol to prepare an isobutanol mixed solution containing 0.49% by mass of acetic acid and 2.39% by mass of isobutyl acetate with respect to isobutanol.

Comparative Example 1

The same operation as in Example 1 was conducted, except that isobutanol (manufactured by Wako Pure Chemical Industries, Ltd., a purity of 99.5%) in which an organic acid and an organic acid ester are not present was used instead of the isobutanol mixed solution.

The results of Examples 1 to 20 and Comparative Example 1 described above are presented in Table 1.

TABLE 1

| | Types of organic acid and organic acid ester | Content of organic acid and organic acid ester [% by mass] | Isobutylene selectivity [%] |
|---|---|---|---|
| Example 1 | Isobutyl acetate | 0.02 | 85.7 |
| Example 2 | Isobutyl acetate | 0.10 | 86.5 |
| Example 3 | Isobutyl acetate | 0.49 | 86.1 |
| Example 4 | Isobutyl acetate | 1.93 | 86.4 |
| Example 5 | Isobutyl acetate | 2.87 | 87.4 |
| Example 6 | Isobutyl acetate | 4.69 | 87.3 |
| Example 7 | Isobutyl acetate | 6.45 | 87.9 |
| Example 8 | Isobutyl acetate | 8.97 | 88.0 |
| Example 9 | tert-Butyl acetate | 4.69 | 89.0 |
| Example 10 | Ethyl acetate | 2.91 | 87.1 |
| Example 11 | Acetic acid | 0.50 | 86.8 |
| Example 12 | Acetic acid | 1.96 | 87.2 |
| Example 13 | Acetic acid | 4.77 | 86.9 |
| Example 14 | Propionic acid | 2.90 | 88.8 |
| Example 15 | Valeric acid | 2.87 | 88.0 |
| Example 16 | Methacrylic acid | 2.92 | 88.1 |
| Example 17 | Methacrylic acid | 1.46 | 88.2 |
| | Ethyl acetate | 1.46 | |
| Example 18 | Acetic acid | 1.46 | 87.8 |
| | Isobutyl acetate | 1.43 | |
| Example 19 | Acetic acid | 2.43 | 88.2 |
| | Isobutyl acetate | 0.48 | |
| Example 20 | Acetic acid | 0.49 | 87.7 |
| | Isobutyl acetate | 2.39 | |
| Comparative Example 1 | — | — | 85.0 |

As presented in Table 1, in Examples 1 to 20, it was possible to produce isobutylene from isobutanol with a high selectivity.

This application claims priority based on Japanese Patent Application No. 2014-136712 filed on Jul. 2, 2014 and the disclosure of which is hereby incorporated in its entirety.

Hereinbefore, the invention of this application has been described with reference to embodiments and Examples. However, the invention of this application is not limited to the above embodiments and Examples. Various changes understandable to those skilled in the art can be made to the configuration and the specifics of the invention of this application without departing from the scope of the invention.

The invention claimed is:

1. A method for producing isobutylene, the method comprising dehydrating isobutanol in a reactor to obtain isobutylene, wherein the dehydrating occurs in the presence of at least one of an organic acid and an organic acid ester, and wherein the content of the organic acid, the organic acid ester, or both the organic acid and the organic acid ester, is 0.005 to 10% by mass with respect to a total of the mass of the isobutanol, the mass of the organic acid, and the mass of the organic acid ester.

2. The method according to claim 1, wherein the content of the organic acid, the organic acid ester, or both the organic acid and the organic acid ester, is 0.02 to 5% by mass with respect to a total of the mass of the isobutanol, the mass of the organic acid, and the mass of the organic acid ester.

3. The method according to claim 1, wherein the organic acid is a carboxylic acid and the organic acid ester is a carboxylate ester.

4. The method according to claim 3, wherein the dehydrating occurs in the presence of at least one carboxylic acid selected from the group consisting of acetic acid. propionic acid, butyric acid, Valerie, acid, and methacrylic acid.

5. The method according to claim 3, wherein the dehydrating occurs in the presence of at least one carboxylate ester selected from the group consisting of an acetate ester, a propionate ester, a butyrate ester, a valerate ester and a methacrylate ester.

6. The method according to claim 1, wherein the dehydrating is performed in the presence of both the organic acid and the organic acid ester.

7. A method for producing methacrylic acid, the method comprising:
   producing isobutylene by the method of claim 1; and
   subjecting the isobutylene to vapor phase catalytic oxidation with molecular oxygen to obtain methacrylic acid.

8. A method for producing methacrylic acid, the method comprising:
   producing isobutylene by the method of claim 1;
   subjecting the isobutylene to hydration in the presence of an acid catalyst to obtain tert-butyl alcohol; and
   subjecting the tent-butyl alcohol to vapor phase catalytic oxidation with molecular oxygen to obtain methacrylic acid.

9. A method for producing methyl methacrylate, the method comprising:
   producing methacrylic acid by the method of claim 7; and
   subjecting the methacrylic acid to an esterification reaction with methanol in the presence of an acid catalyst to obtain methyl methacrylate.

10. A method for producing methyl methacrylate, the method comprising:
    producing methacrylic acid by the method of claim 8; and
    subjecting the methacrylic acid to an esterification reaction with methanol in the presence of an acid catalyst to obtain methyl methacrylate.

11. The method according to claim 1, wherein said dehydrating is performed in the gas phase.

12. The method according to claim 11, wherein said reactor is a fixed bed reactor comprising a catalyst.

13. The method according to claim 11, wherein said reactor is a fluidized bed reactor comprising a catalyst.

14. The method according to claim 12, wherein the temperature of the catalyst during the dehydrating is 108 to 500° C.

15. The method according to claim 12, wherein the temperature of the catalyst during the dehydrating is 150 to 400° C.

16. The method according to claim 13, wherein the temperature of the catalyst during the dehydrating is 108 to 500° C.

17. The method according to claim 13, wherein the temperature of the catalyst during the dehydrating is 150 to 400° C.

18. The method according to claim 15, wherein the dehydrating occurs
    in the presence of at least one carboxylic acid selected from the group consisting of acetic acid, propionic acid, butyric acid, valeric acid, and methacrylic acid, or
    in the presence of at least one carboxy late ester selected from the group consisting of an acetate ester, a propionate ester, a butyrate ester, valerate ester and a methacrylate ester.

19. The method according to claim 17, wherein the dehydrating occurs
    in the presence of at least one carboxylic acid selected from the group consisting of acetic acid, propionic acid, butyric acid, valeric acid, and methacrylic acid, or
    in the presence of at least one carboxylate ester selected from the group consisting of an acetate ester, a propionate ester, a butyrate ester, a valerate ester and a methacrylate ester.

* * * * *